United States Patent [19]
Mori et al.

[11] Patent Number: 5,691,150
[45] Date of Patent: Nov. 25, 1997

[54] IMMUNOASSAY FOR INSULIN-LIKE GROWTH FACTORS

[75] Inventors: Kazumine Mori, Chiba; Shigeto Takasu; Hiroyuki Kasahara, both of Sakura; Shuji Horikawa, Narita, all of Japan

[73] Assignee: Daiichi Radioisotope Laboratories, Ltd., Tokyo, Japan

[21] Appl. No.: 556,397

[22] Filed: Nov. 9, 1995

[30] Foreign Application Priority Data

Nov. 15, 1994 [JP] Japan .................................. 6-304234

[51] Int. Cl.$^6$ ............................ G01N 33/53; G01N 33/48
[52] U.S. Cl. ............................ 435/7.1; 435/975; 436/63; 436/808; 436/826
[58] Field of Search ....................... 435/7.1, 975; 436/63, 436/808, 826

[56] References Cited

FOREIGN PATENT DOCUMENTS

| | | |
|---|---|---|
| 0 100 543 | 2/1984 | European Pat. Off. . |
| 0 292 656 | 11/1988 | European Pat. Off. . |
| 0 392 332 | 10/1990 | European Pat. Off. . |
| 0 492 552 | 7/1992 | European Pat. Off. . |

OTHER PUBLICATIONS

Blum et al, "A specific radioimmunoassay for insulin–like growth factor II: the interference of IGF binding proteins can be blocked by excess IGF–I", Acta Enocrinol., vol. 118, pp. 374–380 1988.

Analytical Biochemistry, vol. 191, No. 1, pp. 75–77, Nov. 15, 1990, Thomas A. Bicsak, et al., "Insulin–Like Growth Factor Binding Protein Measurement: Sodium Dodecyl Sulfate–Stable Complexes with Insulin–Like Growth Factor in Serum Prevent Accurate Assessment of Total Binding Protein Content by Ligand Blotting".

Domestic Animal Endocrinology, vol. 8, No. 3, pp. 393–405, Jul. 1991, K. Plaut, et al., "Evaluation of Interference by Insulin–Like Growth Factor I (IGF–I) Binding Proteins in a Radioimmunoassay for IGF–I in Serum From Dairy Cows".

The Journal of Biological Chemistry, vol. 269, No. 32, pp. 20388–20393, Aug. 12, 1994, T. Arai, et al., "Heparin, Heparan Sulfate, and Dermatan Sulfate Regulate Formation of the Insulin–Like Growth Factor–I and Insulin–Like Growth Factor–Binding Protein Complexes".

Morris, J.C. et al., "Clinical Utility of Thyrotropin–Receptor Antibody Assays: Comparison of Radioreceptor and Bioassay Methods." Mayo Clin. Proc., 63:707–717 (1988).

Journal of Clinical Endocrinology and Metabolism, vol. 54, No. 5, pp. 1084–1086, May 1982, R. Furlanetto, "Pitfalls in the Somatomedin–C Radioimmunoassay".

Journal of Clinical Endocrinology and Metabolism, vol. 56, No. 2, pp. 384–389, Feb. 1983, D. Clemmons, et al., "Liberation of Immunoreactive Somatomedin–C From Its Binding Proteins by Proteolytic Enzymes and Heparin".

Journal of Clinical Endocrinology and Metabolism, vol. 56, No. 2, pp. 376–383, Feb. 1983, P. Chatelain, et al., "Effect of In Vitro Action of Serum Proteases or Exposure to Acid on Measurable Immunoreactive Somatomedin–C in Serum".

*Primary Examiner*—Lila Feisee
*Assistant Examiner*—Yvonne Eyler
*Attorney, Agent, or Firm*—Oblon, Spivak, McClelland, Maier & Neustadt, P.C.

[57] ABSTRACT

Described are immunoassay of insulin-like growth factors in a biological sample, which comprises prior to the immunoassay, treating the biological sample with an acid solution to liberate the insulin-like growth factors from insulin-like growth factor binding proteins and then neutralizing the so-treated biological sample with a neutralizing buffer containing a recombination inhibitor; and immunoassay kit for insulin-like growth factors.

17 Claims, 2 Drawing Sheets

Concentration calculated based on standard solution (ng/ml)

Concentration calculated based on standard solution (ng/mL)

IMMUNOASSAY FOR INSULIN-LIKE GROWTH FACTORS

BACKGROUND OF THE INVENTION

1. Field of the Invention

The present invention relates to an assay for insulin-like growth factors in a biological sample. More specifically, this invention pertains to an immunoassay for the total amount of insulin-like growth factor I (IGF-I) and that of insulin-like growth factor II (IGF-II); and also to a kit therefor. The above total amounts can provide useful information for the medical diagnosis of growth insufficiency diseases such as growth insufficiency, growth hormone aberration and the like.

2. Description of the Related Art

For the medical diagnosis of growth insufficiency diseases such as growth insufficiency, growth hormone aberration and the like, it has conventionally been the practice to measure the amount of growth hormone. Its blood level however fluctuates significantly, thereby making it difficult to use the same for diagnosis. IGF-I which acts for the growth of bones cooperatively with growth hormone and shows reduced fluctuations in its blood level, on the other hand, is known to have high clinical utility for the diagnosis of growth insufficiency diseases, so that it has now become the practice to measure the amount of IGF-I instead of that of growth hormone. IGF-II is known to exist widely in blood and osseous tissues similar to IGF-I. The elucidation of significance of its in vitro existence is therefore eagerly awaited and for this purpose, there is a strong outstanding desire for the accurate assay of the factors.

As conventional measuring methods for insulin-like growth factors (IGFs), the following methods are known. First, radio receptor assay is mentioned, in which the expression of physiological binding activity of IGFs with target cells is directly measured [R. N. Marshall, Journal of Clinical Endocrinology and Metabolism, 39, 283–292(1974); W. H. Daughaday, Journal of Clinical Endocrinology and Metabolism, 53, 282–288 (1981); R. C. Baxter, Journal of Clinical Endocrinology, 24, 267–278]. This method, however, involves difficulty in obtaining uniform receptors for use in measurements, is complex and requires a long reaction time. These drawbacks often produce results which make determination difficult. This radio receptor assay is therefore regarded to have little utility for everyday use in clinical tests.

A competitive immunoassay [Furlanetto, Journal of Clinical Investigation, 60, 648–657(1977)] is also known. According to this method, polyclonal antiserum which is specific and highly-sensitive to insulin-like growth factors (IGFs) is produced and then, IGFs to be measured, $^{125}$I-labeled IGFs and the polyclonal antiserum are reacted at suitable concentrations to make the $^{125}$I-labeled IGFs and IGFs competitively react to the binding sites of the polyclonal antiserum. This method, however, requires many steps and a long reaction time and moreover, involves irksome B/F separation. Such drawbacks have made it difficult for this method to spread in clinical tests where a large number of samples have to be promptly handled.

In the meantime, a technique has been developed to obtain a monoclonal antibody by fusing in vitro immunosensitized-antibody-forming cells and myeloma cells to form a hybridoma [Nature, 256, 495–497(1975)]. The application of this technique has made it possible to mass-produce an antibody protein which is mono-specific to IGFs. Development of radioimmunoassay featuring high specificity and fast reaction was studied using the monoclonal antibody (Japanese Patent Laid-Open No. 3561/1989).

Incidentally, serum is known to contain insulin-like growth factor binding proteins (hereinafter abbreviated as "IGFBPs" or sometimes simply referred to as the "binding proteins") which play an important role in the protection or control of IGF-I and IGF-II. IGFBPs are also known to exist in the form of complexes with IGFs. These binding proteins become a serious interference upon measuring the accurate total amount of IGFs by radioimmunoassay so that separation of IGFs from the binding proteins prior to the measurement is needed as a pre-treatment. As this pre-treatment, gel chromatography under acid conditions, solid-phase extraction (Sep-Pak extraction), acid ethanol extraction or the like has been conventionally employed.

Among these pre-treatment methods, gel chromatography under acid conditions [J. Zapf, Journal of Clinical Investigation, 68, 1321–1330(1981), R. L. Hintz, Journal of Clinical Endocrinology and Metabolism, 45, 988–995 (1977), D. R. Powell, Journal of Clinical Endocrinology and Metabolism, 63, 1186–1192(1986)] is a method in which the binding proteins and IGFs are dissociated through a column by taking advantage of the difference in their molecular weights and the eluate fractions of IGFs so obtained are neutralized for measurement. This method, however, is not suited for everyday clinical tests, because it has difficulty in handling a large number of samples and in addition, it requires an additional equipment for the column.

The solid phase (Sep-Pak) method [W. H. Daughaday, Journal of Laboratory Clinical Medicine, 109, 355–363 (1987)] is a method to separate and quantitate IGFs by using a commercially-available, small-sized column (Sep-Pak) packed with a gel adsorptive to IGFs. This method is, however, not free of irksome operations and is costly so that it is not suited for the treatment of a large number of samples.

The most frequently employed method among the pre-treatment methods is acid ethanol extraction [W. H. Daughaday, Journal of Clinical Endocrinology and Metabolism, 51, 781–788(1980)]. This method comprises blending serum with a hydrochloric acid-ethanol mixed solution, separating IGFs from binding proteins with the acid, precipitating the binding proteins with ethanol of a specific concentration, separating and collecting the supernatant by centrifugal separation, lowering the ethanol concentration in the supernatant so obtained, completely neutralizing and diluting the acid in the supernatant with a neutralizing buffer to buffer the strong acid, and immunologically measuring the diluted solution as a sample.

One of the characteristics of the acid-ethanol extraction lies in that the lowering in the pH of the acid has great effects on the separation of IGFs from the binding proteins. In this method, ethanol is considered to have effects of dissolving and extracting the acid-separated IGFs alone and separating and precipitating the binding proteins remaining in the aqueous solution, thereby inhibiting any recombination of IGFs and the binding proteins into a complex.

The acid ethanol extraction method is most popular in these days. Data of IGF-I measured according to this method are considered to be one of the most important information for the diagnosis and treatment of growth insufficiency diseases in public institutes.

The acid ethanol extraction, however, is accompanied with drawbacks that it requires irksome operations such as centrifugal separation and besides, neutralization of the resulting supernatant is necessary, in other words, it requires irksome operations and also test tubes for the respective operations so that this method is not suited for handling a large number of samples. Another drawback is that upon suction of the supernatant, that is, the acid ethanol solution through a pipette after the centrifugal separation, an error in the sucked amount due to the difference in liquid properties between ethanol and the aqueous solution gives a substantial influence on the measured value and in addition, the suction operation takes much time. Further, an influence of ethanol, the organic solvent used for the extraction, on the immunoassay and depending on the sample, an downward influence of the binding proteins still remaining in the acid-ethanol extract on the measured value have been reported and have posed problems.

Being interested in the binding of IGF-I and IGF-II to similar sites on binding proteins, Blum, et al. reported that immunoassay of IGF-I and IGF-II in serum can be performed in a neutralizing buffer without extraction by, subsequent to the treatment of the sample with an acid (pH 3.1 or lower), adding to the neutralizing buffer excess IGF-I (100 times or greater) in the case of an IGF-II assay system or excess IGF-II in the case of an IGF-I assay system for prevention of recombination with the binding proteins [W. F. Blum, Acta Endocrinologica, 118, 374–380(1988); W. F. Blum, Third International Symposium on Insulin-like Growth Factors, 11–19(1994)]. In short, this method is to inhibit the binding of IGF-I or IGF-II with the binding proteins by adding a so-called analogous IGFs.

For this assay, however, an antibody which has no cross reactivity with IGF-II in the measurement of IGF-I or with IGF-I in the measurement of IGF-II, that is, a highly-specific antibody should be selected for use. A highly-specific antibody which does not cross-react with an analogous IGFs is also indispensable as the primary antibody (trapping antibody) in the sandwich technique. They hence results in the imposition of a substantial limitation on the selection of an antibody. In addition, it is necessary to provide IGF-I and IGF-II in large amounts for their addition to the neutralizing buffer. Upon formation of this assay into a commercial kit, the need for IGF-I and IGF-II in such large amounts would result in a significant increase in cost so that it cannot be an inexpensive assay promising wide spread adoption.

There is accordingly a desire for the development of a simpler and more economical assay for insulin-like growth factors, which needs neither irksome operations nor many equipments and can handle a large number of samples.

SUMMARY OF THE INVENTION

With the forgoing in view, the present inventors have conducted an extensive investigation on the measurement of insulin-like growth factors. As a result, it has been found that the recombination of insulin-like growth factors with insulin-like binding proteins can be inhibited by treating a biological sample with an acid solution, liberating the insulin-like growth factors from the insulin-like binding proteins and then using a neutralizing buffer containing a specific substance, and that the sample so obtained can be used, as is, for imanunoassay, leading to the completion of the present invention.

An object of the present invention is therefore to provide an immunoassay for insulin-like growth factors in a biological sample, which comprises prior to the immunoassay, treating the biological sample with an acid solution to liberate the insulin-like growth factors from insulin-like growth factor binding proteins and then neutralizing the biological sample with a neutralizing buffer containing therein a recombination inhibitor.

Another object of the present invention is to provide a kit for the immunoassay of insulin-like growth factors in a biological sample, said kit being useful for the above immunoassay.

The present invention has made it possible to handle a large amount of biological samples without irksome operations or many equipments and to assay insulin-like growth factors more simply and economically at high accuracy.

In the present invention, each biological sample is prepared without using ethanol, that is, an organic solvent so that adverse effects such as a reduction in accuracy or binding are not given to the immunoassay system, thereby bringing about a marked advantage over the conventional acid-ethanol-extraction method. In addition, the immunoassay according to the present invention can be conducted on a sample in the form of an aqueous solution in which IGF and binding proteins are contained together. This has substantially simplified the operations compared with the conventional acid-ethanol extraction immunoassay which requires separation of IGFs from binding proteins prior to the measurement.

Further, the immunoassay according to the present invention neither forces use of glass-made test tubes nor requires centrifugal separation so that a large number of samples can be handled and a reduction in the initial cost for clinical tests can also be facilitated.

Furthermore, ANS or the like which is a recombination inhibitor useful in the present invention has advantages that it is inexpensive, does not require any expensive reagent as an additive and that it imposes a smaller restriction upon selection of an antibody.

Some samples which have heretofore been considered to have low extraction rates when assayed according to the conventional acid-ethanol-extraction method have been found to give high values when measured by the immunoassay according to the present invention. This has been brought about owing to high extraction rates available from the practice of the immunoassay according to the present invention. This has proven that the assay according to the present invention is a method permitting full extraction of IGFs and accurate measurement of total IGF.

DETAILED DESCRIPTION OF THE PREFERRED EMBODIMENTS

Figure 1:
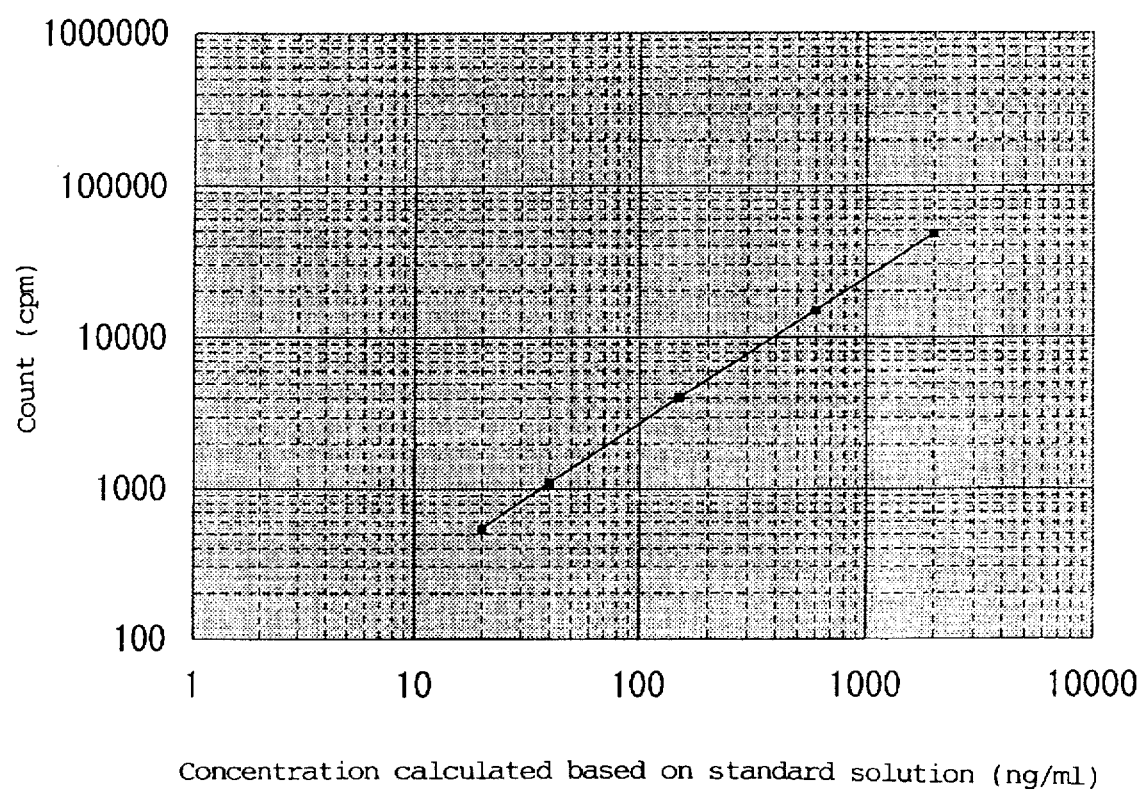
FIG. 1 diagramatically shows a standard curve obtained according to the immunoassay of the present invention with respect to IGF-II.

To practice the immunoassay according to present invention, it is necessary to treat a biological sample, which is to be assayed, with an acid solution to liberate IGFs from the binding proteins, to neutralize the so-treated biological sample with a neutralizing buffer containing a recombination inhibitor and then to perform the immunoassay of IGFs in a manner known per se in the art.

Examples of the biological sample usable in the present invention as a system for the immunoassay of the total IGF amount include IGF-containing biological fluids such as serum, plasma, urine, ascites, pleural exudate, whey, amniotic effusion, spinal fluid, biological extract and biological exudate.

Illustrative of the acid solution used for the liberation of IGFs from the binding proteins include solutions such as hydrochloric acid, sulfuric acid, phosphoric acid, formic acid, trifluoroacetic acid and trichloroacetic acid; and their buffers with glycine, citric acid, acetic acid, salicylic acid or the like.

This acid solution can be used preferably in an amount 5 to 100 times as much as the biological sample and the resulting acid-treated biological sample can preferably have a pH of 3.5 or lower, particularly of 3.0 or lower.

No particular limitation is imposed on the recombination inhibitor to be added to the neutralizing buffer insofar as it is a substance having an affinity with the IGF binding proteins. Preferred examples include 8-anilino-1-naphthalenesulfonic acid (ANS), salicylic acid, sodium dodecyl sulfate (SDS) and heparin and salts thereof. These recombination inhibitors are effective even when used singly, but more effective when used in a suitable combination. A combination of ANS and salicylic acid can be selected as a preferred illustrative combination.

The neutralizing buffer used in the present invention is a buffer which has a pH ranging from 6.0 to 10. Examples include phosphate buffer, carbonate buffer, glycine buffer, barbital buffer, tris buffer, bistris buffer and the like.

It is only necessary for the buffer to be adjusted in concentration and amount so that the biological sample diluted and treated with the acid solution as described above can be fully neutralized.

The amount of the recombination inhibitor to be added to the neutralizing buffer varies depending on the kind of the inhibitor. For example, it is preferred to add the inhibitor in an amount of about 0.01 to 0.30% when ANS-Mg or another ANS salt is used as the inhibitor, in an amount of about 0.1 to 3.0% when sodium salicylate is used, in an amount of about 0.001% to 0.02% when SDS is used, all based on the neutralizing buffer; and in an amount of about 1 to 50 U/ml when heparin is used. Although the recombination inhibitor may be added to the neutralizing buffer upon use, it is advantageous from the standpoint of improved work efficiency to add it to the neutralizing buffer in advance so that the neutralizing buffer and the recombination inhibitor can be furnished in the form of a composition.

In the present invention, the neutralized sample with the recombination inhibitor contained therein can be used, as is, for the immunoassay. No particular limitation is imposed on the manner of immunoassay to be adopted. Examples include immunoassays employing various labeling methods such as radioimmunoassay, enzyme immunoassay, immunofluorescence assay, chemiluminescence assay and the like, each being conducted by the competitive technique or double antibody sandwich technique. These immunoassays can be performed in a manner known per se in the art.

When the sandwich technique is adopted for the above immunoassays, either the combination of a labeled liquid-phase antibody and a solid-phase antibody or the combination of a labeled liquid-phase antibody and a liquid-phase antibody can be used. The former combination is, however, preferred from the viewpoint of operability. Exemplary labeling methods usable in the present invention include labeling with a radioisotope such as $^{125}I$ or the like while using an oxidizing agent such as chloramine T or the like, labeling with an enzyme such as alkaline phosphatase or peroxidase by the hinge method or the like, and directly labeling with a fluorescent substance such as europium or an luminescent substance such as acridinium ester.

To advantageously practice the above-described immunoassay for IGFs according to the present invention, an IGF assay kit containing the reagents as shown below can be used for example.

(a) a neutralizing buffer containing a recombination inhibitor.

(b) a labeled anti-IGF antibody.

(c) a solid-phase anti-IGF antibody.

Among these, the component (a) may be in the form of a lyophilized product which is added with water upon use. As the label in the component (b), a known radioisotope, enzyme, fluorescent substance or a chemiluminescent substance can be used. Regarding the component (c), the conversion into the solid phase can be conducted using an insoluble substance such as glass, plastic, fine particles or fine porcelain particles. The component (c) can take the form of a wall of a vessel such as a tube, beads, proteinaceous fine particles, iron-made fine particles or the like.

The above kit according to the present invention can further comprise an acid solution for the liberation of IGFs from the binding proteins.

In the present invention, the acid solution plays a role of weakening the bonding between the insulin-like growth factors (IGF-I, IGF-II) and the insulin-like growth factor binding proteins (IGFBP-1 to 6), thereby separating IGFs from the binding proteins.

If the sample treated with the acid solution is neutralized with a buffer alone, IGFs inevitably reconstitutes complexes with the binding proteins. When the neutralization is conducted, on the other hand, in the presence of a recombination inhibitor such as ANS, salicylic acid, SDS, heparin or the like or a salt thereof as described above, the recombination inhibitor bonds to the IGF-binding sites of the IGF binding proteins or by using its steric hindrance, can prevent recombination of the binding proteins with IGFs, thereby making it possible to conduct an accurate measurement on IGFs.

Described specifically, a biological sample is treated under acid conditions and then added with a neutralizing buffer containing, as a recombination inhibitor, ANS, salicylic acid, SDS or heparin or a salt thereof to neutralize the same, whereby a sample suited for immunoassay is prepared.

The present invention will next be described more specifically by the following Examples. It should however be borne in mind that this invention is by no means limited to or by the examples.

EXAMPLE 1

Preparation of reagents for the radioimmunoassay of IGF-II and radioimmunological quantitation (1) Procurement of IGF-II antibody Various mouse-hybridoma-derived IGF-II antibodies were produced using BSA-IGF-II conjugates as immuno sources by a method known per se in the art, and 6B was selected as a clone of the highest affinity by making use of the antigen-antibody reaction known per se in the art. Hybridoma 1D5 (Japanese Patent Laid-Open No. 252987/1993) which had been produced in a similar manner was obtained from DAIICHI PHARMACEUTICAL CO., LTD. and was provided for use.

These two kinds of clones were allowed to proliferate in mouse ascites. They were salted out with saturated sodium sulfate, followed by gel filtration ["TSKG3000 SWXL", trade name; 0.05M-$NaPO_4$/0.1M-$Na_2PO_4$, pH6.4) to obtain antibody fractions. The antibody fractions so obtained were purified by ion exchange (monoQ, 20 mM-tris, pH 8.0), followed by concentration and dialysis against a phosphate buffer (20 mM, pH 7.4). These two clones, 1D5 and 6B, were prepared at final concentrations of 8.7 mg/ml and 2.6 mg/ml, respectively.

These anti-IGF monoclonal antibodies each had a purity of 95% or greater as measured by HPLC. According to the Scatchard plot analysis, 1D5 and 6B were found to have affinity constants of $0.9 \times 10^8$ L/Mol and $2 \times 10^9$ L/Mol and also to be classified as subtypes IgG1 and IgG2a, respectively.

(2) Preparation of $^{125}$I-labeled anti-IGF-II antibody

In a silicone-coated glass tube, 2.6 mCi of NEN-made Na$^{125}$I were charged, followed by the addition of 196 μl (500 μg) of a solution of the above 6B monoclonal anti-IGF-II antibody (MoAb-6B) and then 30 μg/10 μl (H$_2$O) of chloramine T. After the resulting mixture was stirred for 20 seconds for reaction, 60 μg/10 μl (H$_2$O) of sodium metabisulfite were added to the reaction mixture to terminate the reaction.

The reaction mixture so obtained was then loaded on a "Sephacryl S-300 Column" (trade name; 1.0 cm in diameter, 45 cm in length) which had been equilibrated sufficiently with a 0.1M tris-HCl buffer (pH 7.4) containing 0.5% BSA and 0.1% NaN$_3$. Eluate from the column was fractionated 1 ml by 1 ml. In total, 20 to 22 ml were allowed to elute from the column and the immunoactivity of each fraction at a peak position of high radioactivity was measured to confirm the position of the target labeled antibody. The fractions so obtained were pooled as a purified reaction mixture.

The labeling rate of the reaction mixture as determined by paper chromatography was 90%. Accordingly, the specific radioactivity was 5.9 μCi/μg ($2620~\mu Ci \times 0.90 \div 500 \div 0.8 = 5.9$ μCi/μg, 0.8: counting efficiency of a counter).

The purified reaction mixture was diluted with a phosphate buffer (100 mM, pH 7.4) containing 0.1% gelatin and 0.1% "Tween #20" (trade name), whereby a $^{125}$I-labeled anti-IGF-II antibody reagent having a final radioactivity of about 14.3 kBq (0.39 μCi/ml) was prepared (the amount of the reagent to be used for the assay was, however, about 2.9 kBq/200 μl/tube).

(3) Preparation of anti-IGF-II-antibody-coated beads

In a glass beaker, polystyrene beads of 6 mm in diameter and 0.4 ml/bead of a 5% detergent solution were charged, followed by stirring with a stirrer bar to remove the burrs and the like from the surfaces of the beads. The beads were washed five times with deionized water to remove the detergent solution. To the beads, a 1 mM phosphate buffer (pH 5.9) containing μg/0.2 ml/bead of the 1D5 monoclonal anti-IGF-II antibody (MoAb-1D5) was added, followed by gentle stirring overnight at 25° C. to make the beads adsorb the antibody. The antibody-adsorbed beads were each washed twice with deionized water, followed by the addition of 0.2 ml/bead of a 25 mM phosphate buffer (pH 7.4) containing 0.2M magnesium sulfate (7 hydrate), 0.5M NaCl and 0.5% BSA. The resultant mixture was then allowed to stand for 3 hours. The buffer was removed from the reaction mixture, followed by drying overnight, whereby antibody-coated beads were obtained.

(4) Preparation of standard IGF-II, pretreatment solution and neutralizing buffer Standard IGF-II was prepared by adjusting "Recombinant IGF-II" (trade name; product of DAIICHI PHARMACEUTICAL CO., LTD.), for which a recombinant DNA was employed, to an appropriate concentration with a 100 mM phosphate buffer (pH 7.4) containing 0.1% NAN$_3$, 0.1% EDTA2Na and 0.5% BSA.

As the pretreatment solution, an acid solution of 25 mM glycine hydrochloride (pH 1.5) was used.

As the neutralizing buffer, a 200 mM tris-HCl buffer (pH 8.0) containing 0.08% of ANS-Mg (8-anilino-1-naphthalenesulfonic hemimagnesium), 0.5% of gelatin, 0.1% of "Tween #20" (trade name) and 0.1% of NaN$_3$ was prepared and provided.

(5) Radioimmunoassay of the total serum IGF-II amount and its results

In glass test tubes or polystyrene test tubes, 1.0 ml portions of the pretreatment solution were added to 25 μl of serums as samples to be assayed (Samples Nos. 1 to 7), respectively. After vigorous stirring, the reaction mixtures were allowed to stand.

Each acid-diluted sample (50 μl) treated with the pretreatment solution or 50 μl of standard IGF-II which had been adjusted to an appropriate concentration were charged in a newly-provided polystyrene tube, followed by the addition of 300 μl of the neutralizing buffer to neutralize and buffer the acid. The resulting mixture was added with one of the antibody-coated beads, followed by shaking at room temperature for 2 hours.

After the completion of the primary reaction, the reaction mixture was removed by suction. The tube was then washed twice with 2 ml/tube of physiological saline. To the tube, 0.2 ml/tube of $^{125}$I-labeled anti-IGF-II antibody solution was added, followed by shaking at room temperature for one hour. After the completion of the reaction, the reaction mixture was removed by suction. After the tube was washed twice with 2 ml/tube of physiological saline, the radioactivity of each tube was measured.

Upon assay, the concentration of IGF-II was read from the radioactivity of the diluted sample by using a standard curve (Table 1 and FIG. 1) plotted based on radioactivities of the standard IGF-II and the concentrations (converted concentrations) obtained by multiplying its actual concentrations by 41, the rate of dilution of the sample in terms of times.

For comparison, the samples (Nos. 1–7) were treated in a similar manner except that the acid-ethanol extraction was employed.

The results are shown in Table 2.

TABLE 1

| Concentration calculated based on standard solution (ng/ml) | Count (cpm) | B/T (%) | CV (%) |
|---|---|---|---|
| Total | 129456 | | |
| 0 | 220 | 0.2 | 9.7 |
| 20 | 539 | 0.4 | 4.1 |
| 40 | 1102 | 0.9 | 2.3 |
| 150 | 4050 | 3.1 | 3.4 |
| 600 | 14982 | 11.6 | 5.4 |
| 2000 | 47776 | 36.9 | 0.5 |

TABLE 2

| Sample No. of sample | Assay result (ng/ml) | | Invention method/ Comparative method (%) |
|---|---|---|---|
| | Comparative method* | Invention method | |
| 1 | 806.9 | 818.2 | 101 |
| 2 | 486.7 | 581.2 | 119 |
| 3 | 424.1 | 501.2 | 118 |
| 4 | 588.2 | 607.5 | 103 |
| 5 | 556.0 | 653.5 | 118 |

TABLE 2-continued

|  | Assay result (ng/ml) | | Invention method/ |
|---|---|---|---|
| Sample No. of sample | Comparative method* | Invention method | Comparative method (%) |
| 6 | 425.1 | 486.8 | 115 |
| 7 | 570.4 | 628.2 | 110 |

*In the column under "Comparative method", assay results by the acid-ethanol extraction are shown.

EXAMPLE 2

Preparation of reagents for radioimmunoassay of IGF-I and radioimmunological quantitation (1) Procurement of IGF-I antibody Various mouse-hybridoma-derived IGF-I antibodies were produced in a manner known per se in the art by using BSA-IGF-I conjugates as immuno sources. Two kinds of clones, 2D and 6B, were selected as clones of highest affinity by making use of the antigen-antibody reaction known per se in the art.

These two kinds of clones were allowed to proliferate in mouse ascites. They were salted out with saturated sodium sulfate, followed by gel filtration ("TSKG3000 SWXL", trade name; 0.05M-NaPO$_4$/0.1M-Na$_2$PO$_4$; pH 6.4), whereby antibody fractions were obtained. The antibody fractions were purified by ion exchange (monoQ, 20 mM-tris, pH 8.0), followed by concentration and dialysis against a phosphate buffer (20 mM, pH 7.4). These two clones, 2D and 6B, were prepared at final concentrations of 7.5 mg/ml and 2.6 mg/ml, respectively.

These anti-IGF-II monoclonal antibodies each had an antibody purity of 95% or greater as measured by HPLC. According to the Scatchard plot analysis, 2D and 6B were found to have affinity constants of $7.2 \times 10^8$ L/Mol and $3.2 \times 10^9$ L/Mol and also to be classifiable as subtypes IgG1 and IgG2a, respectively.

(2) Preparation of $^{125}$I-labeled anti-IGF-I antibody

In a silicone-coated glass tube, 2.6 mCi of NEN-made Na$^{125}$I were charged, followed by the addition of 196 μl (500 μg) of a solution of the above 6B monoclonal anti-IGF-I antibody (MoAb-6B) and then 30 μg/10 μl (H$_2$O) of chloramine T. The resulting mixture was stirred for 20 seconds for reaction. Then, 60 μg/10 μl (H$_2$O) of sodium metabisulfite were added to the reaction mixture to terminate the reaction.

The reaction mixture so obtained was loaded to "Sephacryl S-300 Column" (trade, name; 1.0 cm in diameter, 45 cm in length) which had been equilibrated sufficiently with a 0.1M tris-HCl buffer (pH 7.4) containing 0.5% BSA and 0.1% NaN$_3$. Eluate from the column was fractionated 1 ml by 1 ml. In total, 20 to 22 ml were allowed to elute from the column and the immunoactivity of each fraction at a peak position of high radioactivity was measured to confirm the position of the target labeled antibody. The fractions so obtained were pooled as a purified reaction mixture.

The labeling rate of the reaction mixture as determined by paper chromatography was 90%. Accordingly, the specific radioactivity was 5.9 μCi/μg (2620 μCi×0.90÷500÷0.8=5.9 μCi/μg, 0.8: counting efficiency of a counter).

The reaction mixture so obtained was diluted with a phosphate buffer (100 mM, pH 7.4) containing 0.1% gelatin and 0.1% "Tween #20" (trade name), whereby a $^{125}$I-labeled anti-IGF-I antibody reagent having a final radioactivity of about 14.3 kBq (0.39 μCi/ml) was prepared (an amount used for the assay is, however, about 2.9 kBq/200 μl/tube).

(3) Preparation of anti-IGF-I-antibody-coated beads

In a glass beaker, polystyrene beads of 6 mm in diameter and 0.4 ml/bead of a 5% detergent solution were charged, followed by stirring with a stirrer bar to remove the burrs and the like from the surfaces of the beads. The beads were washed five times with deionized water to remove the detergent solution. To the beads, a 1 mM phosphate buffer (pH 5.9) containing 5 μg/0.2 ml/bead of the 2D monoclonal anti-IGF-I antibody (MoAb-2D) was added, followed by gentle stirring overnight at 25° C. to make the beads adsorb the antibody. The antibody-adsorbed beads were each washed twice with deionized water, followed by the addition of 0.2 ml/bead of a 25 mM phosphate buffer (pH 7.4) containing 0.2M magnesium sulfate (7 hydrate), 0.5M NaCl and 0.5% BSA. The resultant mixture was then allowed to stand for 3 hours. The buffer was removed from the reaction mixture, followed by drying overnight, whereby antibody-coated beads were obtained.

(4) Preparation of standard IGF-I, pretreatment solution and neutralizing buffer Standard IGF-I was prepared by adjusting "Recombinant IGF-I" (trade name; product of Toyobo Co., Ltd.) for which a recombinant DNA was used, to an appropriate concentration with a 100 mM tris-HCl buffer (pH 6.0) containing 0.1% NaN$_3$ and 0.5% BSA.

As the pretreatment solution, an acid solution of 25 mM glycine hydrochloride (pH 1.5) was used.

As the neutralizing buffer, a 200 mM tris-HCl buffer (pH 9.0) containing 0.12% of ANS-Mg (8-anilino-1-naphthalenesulfonic hemimagnesium), 1.0% of sodium salicylate, 0.5% of gelatin, 0.1% of "Tween #20" (trade name) and 0.1% of NaN$_3$ was prepared and provided.

(5) Assay of the total serum IGF-I amount and its results

In glass test tubes or polystyrene test tubes, 1.0 ml portions of the pretreatment solution were added to 25 μl of serums as samples to be assayed (Samples Nos. 1–7), respectively. After vigorous stirring, the reaction mixtures were allowed to stand.

Each acid-diluted sample (50 μl) treated with the pretreatment solution of 150 μl of standard IGF-I which had been adjusted to an appropriate concentration were charged in a newly-provided polystyrene tube, followed by the addition of 300 μl of the neutralizing buffer to neutralize and buffer the acid. The resulting mixture was added with one of the antibody-coated beads, followed by shaking at room temperature for 2 hours.

After the completion of the primary reaction, the reaction mixture was removed by suction. The tube was then washed twice with 2 ml/tube of physiological saline. To the tube, 0.2 ml/tube of $^{125}$I-labeled anti-IGF-I antibody solution was added, followed by shaking at room temperature for one hour. After the completion of the reaction, the reaction mixture was removed by suction. After the tube was washed twice with 2 ml/tube of physiological saline, the radioactivity of each tube was assayed.

Figure 2:
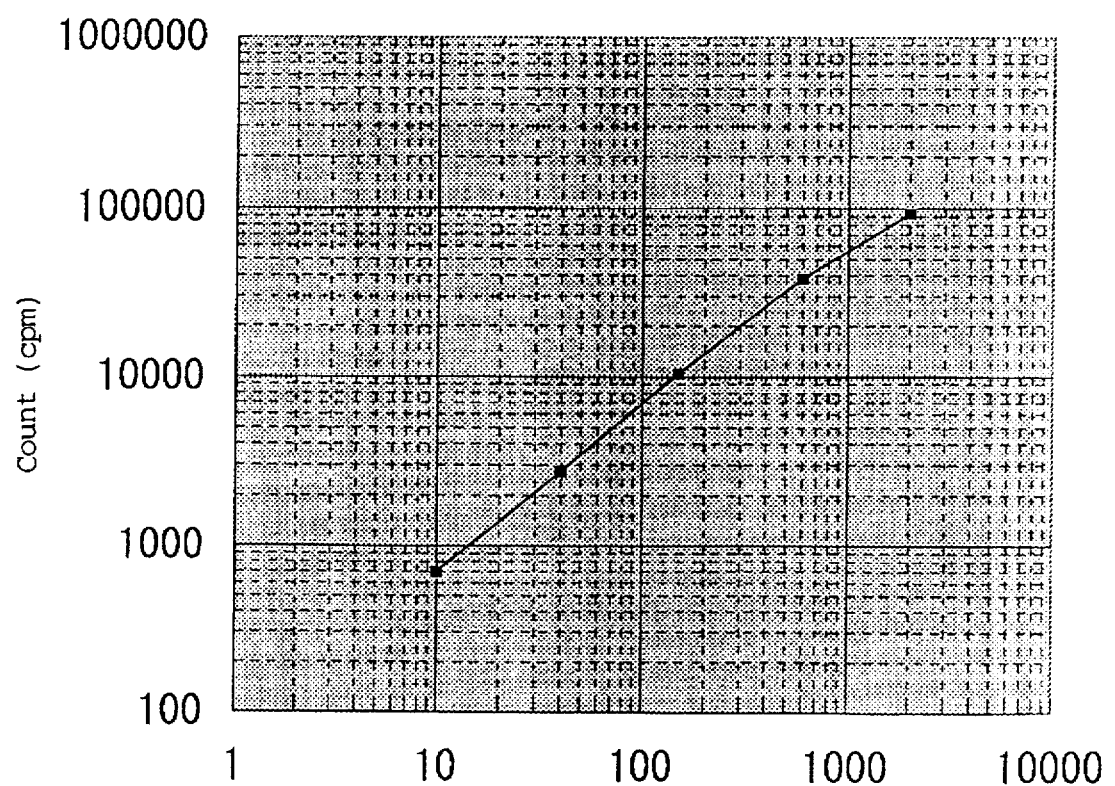
FIG. 2 diagramatically shows a standard curve obtained according to the immunoassay of the present invention with respect to IGF-I.

Upon assay, the concentration of IGF-II was read from the radioactivity of the diluted sample by using a standard curve (Table 3 and FIG. 2) plotted based on radioactivities of the standard IGF-I and the concentrations (converted concentrations) obtained by multiplying its actual concentrations by 41, the rate of dilution of the sample in terms of times.

For comparison, the same samples (Nos. 1–7) were treated in a similar manner except that the acid-ethanol extraction was employed.

The results are shown in Table 4.

TABLE 3

| Concentration calculated based on standard solution (ng/ml) | Count (cpm) | B/T (%) | CV (%) |
|---|---|---|---|
| Total | 128822 | | |
| 0 | 372 | 0.3 | 1.5 |
| 10 | 702 | 0.5 | 4.1 |
| 40 | 2743 | 2.1 | 1.2 |
| 150 | 10393 | 8.1 | 0.0 |
| 600 | 38161 | 29.6 | 1.3 |
| 2000 | 93033 | 72.2 | 0.5 |

TABLE 4

| Sample No. of sample | Assay result (ng/ml) Comparative method* | Assay result (ng/ml) Invention method | Invention method/ Comparative method (%) |
|---|---|---|---|
| 1 | 121.3 | 134.6 | 111 |
| 2 | 9.8 | 11.4 | 117 |
| 3 | 236.8 | 238.0 | 101 |
| 4 | 131.5 | 132.6 | 101 |
| 5 | 166.6 | 170.0 | 102 |
| 6 | 54.4 | 58.6 | 108 |
| 7 | 364.3 | 364.0 | 100 |

*In the column under "Comparative method", assay results by the acid-ethanol extraction are shown.

What is claimed is:

1. An immunoassay for the insulin-like growth factors, IGF-I or IGF-II, or both in a biological sample, which comprises:
   (a) treating a biological sample with an acid solution to liberate IGF-I or IGF-II or both from binding proteins therefor;
   (b) neutralizing the acid treated biological sample with a neutralizing buffer containing a recombination inhibitor other than IGF-I or IGF-II; and
   (c) conducting an immunoassay for IGF-I or IGF-II or both;
   wherein purification of the liberated IGF-I or IGF-II of both from the binding proteins therefor is not required.

2. The immunoassay according to claim 1, wherein the acid solution is hydrochloric acid, sulfuric acid, phosphoric acid, formic acid, trifluoroacetic acid or trichloroacetic acid, or a buffer thereof with glycine, citric acid, acetic acid or salicylic acid.

3. The immunoassay according to claim 1, wherein the recombination inhibitor is 8-anilino-1-naphthalene-sulfonic acid, salicylic acid, sodium dodecyl sulfate or heparin or a salt thereof.

4. The immunoassay according to claim 1, wherein the neutralizing buffer is a phosphate buffer, carbonate buffer, glycine buffer, barbital buffer, tris buffer or bistris buffer.

5. The immunoassay according to claim 1, wherein the biological sample is serum, blood plasma, urine, ascites, fluid in the thoracic cavity, whey, amniotic effusion, spinal fluid, a biological extract or a biological exudate.

6. The immunoassay according to claim 1, which is a radioimmunoassay, enzyme immunoassay, immunofluorescence assay or chemiluminescence assay making use of a competitive technique or double antibody sandwich technique.

7. The immunoassay according to claim 1, wherein about 5 to 100 times the amount of acid solution is used per the amount of biological sample used.

8. The immunoassay according to claim 1, wherein the neutralizing buffer has a pH of from about 6 to 10.

9. The immunoassay according to claim 3, wherein said recombination inhibitors are used in combination.

10. A process for the preparation of a biological sample for the detection of the insulin-like growth factors, IGF-I or IGF-II or both, which comprises:
    (a) treating the biological sample with an acid solution to liberate IGF-I or IGF-II or both from binding proteins therefor; and
    (b) neutralizing the acid treated biological sample in the presence of a recombination inhibitor other than IGF-I or IGF-II; and
    wherein purification of the liberated IGF-I or IGF-II or both from the binding proteins therefor is not required.

11. The process according to claim 10, wherein the acid solution is hydrochloric acid, sulfuric acid, phosphoric acid, formic acid, trifluoroacetic acid or trichloroacetic acid, or a buffer thereof with glycine, citric acid, acetic acid or salicylic acid.

12. The process according to claim 10, wherein the recombination inhibitor is 8-anilino-1-naphthalene-sulfonic acid, salicylic acid, sodium dodecyl sulfate or heparin or a salt thereof.

13. The process according to claim 10, wherein the neutralizing buffer is a phosphate buffer, carbonate buffer, glycine buffer, barbital buffer, tris buffer or bistris buffer.

14. The process according to claim 10, wherein the biological sample is serum, blood plasma, urine, ascites, fluid in the thoracic cavity, whey, amniotic effusion, spinal fluid, a biological extract or a biological exudate.

15. The process according to claim 10, wherein about 5 to 100 times the amount of acid solution is used per the amount of biological sample used.

16. The process according to claim 10, wherein the neutralizing buffer has a pH of from about 6 to 10.

17. The process according to claim 10, wherein said recombination inhibitors are used in combination.

* * * * *